United States Patent [19]

Sikkenga et al.

[11] Patent Number: 5,292,934
[45] Date of Patent: Mar. 8, 1994

[54] METHOD FOR PREPARING AROMATIC CARBOXYLIC ACIDS

[75] Inventors: David L. Sikkenga, Wheaton; George E. Kuhlmann, Naperville; Paul K. Behrens, Warrenville; Martin A. Zeitlin, Naperville; Stephen V. Hoover, Aurora, all of Ill.

[73] Assignee: Amoco Corporation, Chicago, Ill.

[21] Appl. No.: 900,593

[22] Filed: Jun. 18, 1992

[51] Int. Cl.$^5$ .................. C07C 51/23; C07C 51/265; C07C 51/487
[52] U.S. Cl. ................................ 562/413; 562/421; 562/487
[58] Field of Search .................... 562/413, 421, 487

[56] References Cited

U.S. PATENT DOCUMENTS

| | | | |
|---|---|---|---|
| 3,171,856 | 3/1965 | Kurtz | 562/487 |
| 3,644,507 | 2/1972 | Witt et al. | 562/487 |
| 3,717,674 | 2/1973 | Blay | 562/487 |
| 3,862,218 | 1/1975 | Stauzenberger | 562/487 |
| 5,149,867 | 9/1992 | Chen et al. | 562/486 |

FOREIGN PATENT DOCUMENTS 0432910 6/1991 European Pat. Off.
486008 9/1975 U.S.S.R.

Primary Examiner—José G. Dees
Assistant Examiner—Vera C. Clarke
Attorney, Agent, or Firm—Thomas E. Nemo; Wallace L. Oliver

[57] ABSTRACT

Disclosed is a method for preparing an aromatic carboxylic acid comprising oxidizing in the liquid phase an aromatic feed compound containing at least one alkyl or acyl group with a molecular oxygen-containing gas, in a solvent comprising a low molecular weight aliphatic carboxylic acid, and in the presence of a heavy metal oxidation catalyst, thereby forming an oxidation reaction product mixture comprising an aromatic carboxylic acid; subsequently heating the oxidation reaction product mixture at a temperature of at least about 500° F. to form a second product mixture; and recovering from the second product mixture the aromatic carboxylic acid. The method of this invention provides for purer, larger particle size aromatic carboxylic acid product.

23 Claims, 1 Drawing Sheet

METHOD FOR PREPARING AROMATIC CARBOXYLIC ACIDS

FIELD OF THE INVENTION

This invention relates generally to a method for preparing aromatic carboxylic acids. More particularly, this invention relates to an improved method for preparing aromatic carboxylic acids by the liquid phase oxidation of an alkyl or acyl substituted aromatic feed compound.

BACKGROUND OF THE INVENTION

Aromatic carboxylic acids are highly useful organic compounds. Some are used as intermediates for the preparation of other organic compounds, and some are used as monomers for the preparation of polymeric materials. For example, terephthalic acid is used to prepare polyethylene terephthalate, a widely used polyester material and the naphthalenecarboxylic acids (i.e. the naphthoic acids) are used for preparing photographic chemicals and dyestuffs. Additionally, naphthalenedicarboxylic acids can be used to prepare a variety of polyester and polyamide compositions. One such naphthalenedicarboxylic acid, 2,6-naphthalenedicarboxylic acid, is a particularly useful aromatic carboxylic acid because it can be reacted with ethylene glycol to prepare poly(ethylene-2,6-naphthalate) (PEN). Fibers and films manufactured from PEN display improved strength and superior thermal properties relative to other polyester materials such as polyethylene terephthalate. High strength fibers made from PEN can be used to make tire cord, and films made from PEN are advantageously used to manufacture magnetic recording tape and components for electronic applications.

In order to prepare high quality PEN most suitable for the aforementioned applications, it is desirable to use purified 2,6-naphthalenedicarboxylic acid. Similarly, it is desirable to use purified forms of other aromatic carboxylic acids when using these compounds for the hereinabove mentioned applications.

Aromatic carboxylic acids, and particularly 2,6-naphthalenedicarboxylic acid, are conveniently prepared by the liquid phase, metal catalyzed oxidation of an alkyl or acyl substituted aromatic compound. During this oxidation, the alkyl group (for example a methyl, ethyl or isopropyl group) or acyl group is oxidized to a carboxylic acid group. Although this is an effective oxidation reaction it nevertheless has some drawbacks. For example, when a 2-alkyl or 2-acyl substituted naphthalene compound is oxidized, the naphthalene ring itself is susceptible to oxidation and trimellitic acid is produced. Incomplete oxidation of a methyl group produces an aldehyde group instead of a carboxylic acid group. Furthermore, when a promoter such as bromine is used during the liquid phase oxidation, brominated aromatic carboxylic acids are produced. Although all of these impurities are undesirable, trimellitic acid is particularly troublesome because it tends to complex tightly to the metal oxidation catalysts. Such complexed metal is difficult to remove from the aromatic carboxylic acids and, additionally, any process streams containing trimellitic acid are not readily returned to the oxidation reaction mixture because the trimellitic acid complexes to and consequently deactivates the oxidation metal catalysts. Such a recycle stream may originate from oxidation reaction mixture mother liquor that is separated from the aromatic carboxylic acid after the alkyl or acyl group is oxidized. Such recycle stream can also be a wash stream that is formed by washing the aromatic carboxylic acid with a suitable solvent. Thus, a method that provides for an aromatic carboxylic acid having a reduced level of trimellitic acid and/or other impurities, or that reduces the level of trimellitic acid in a process stream so that it can be more effectively recycled to the oxidation reaction mixture is desirable. The present invention provides such a method.

SUMMARY OF THE INVENTION

This invention is a method for preparing an aromatic carboxylic acid comprising a) oxidizing in the liquid phase an aromatic compound having at least one oxidizable alkyl or acyl group with an oxygen containing gas, in a solvent comprising a low molecular weight carboxylic acid, in the presence of a heavy metal oxidation catalyst, and at a reaction temperature of about 250° F. to about 450° F., thereby forming an oxidation reaction product mixture comprising an aromatic carboxylic acid; subsequently b) heating the oxidation reaction product mixture at a temperature of at least about 500° F. thereby forming a second product mixture; and c) recovering from the second product mixture the aromatic carboxylic acid.

In the first step in the method of this invention, the aromatic compound containing at least one oxidizable alkyl or acyl group is oxidized until at least 90% mole percent and preferably until substantially all of the oxidizable alkyl and/or acyl groups are oxidized to carboxylic acid groups thereby forming an aromatic carboxylic acid. In a subsequent step, the resulting product mixture is heat treated at a high temperature of at least about 500° F. Surprisingly, it has been discovered that this procedure provides for a purer form of aromatic carboxylic acid isolated from the oxidation reaction mixture. Additionally, the mixture remaining after the desired aromatic carboxylic acid is recovered, commonly referred to as the mother liquor, has either a reduced level of impurities and byproducts, or contains impurities and byproducts that are less detrimental for recycle to the liquid phase oxidation reaction, thereby facilitating the recycle of mother liquor to the oxidation reaction mixture. It is desirable to recycle mother liquor because it contains useful oxidation catalyst metals, and also because it contains oxidation intermediates that can be oxidized to the desired aromatic carboxylic acid.

The method of this invention is particularly suitable for the oxidation of a dialkyl-, an alkyl-acyl- or diacyl-naphthalene compound to the corresponding naphthalenedicarboxylic acid. The heavy metal catalyzed, liquid phase oxidation of such naphthalene compounds typically requires a high level of metal catalysts, and the oxidation reaction produces trimellitic acid as a reaction byproduct. The method of this invention, however, greatly reduces the level of trimellitic acid in the oxidation reaction product mixture thereby allowing for the recycle of a greater amount of mother liquor to the oxidation reaction. The recycled mother liquor contains—in addition to the valuable oxidation catalyst metals—fine particles of the naphthalenedicarboxylic acid, oxidation intermediates that can be oxidized to naphthalenedicarboxylic acids, and oxidation solvent. Thus, recycle saves these valuable components and also eliminates waste disposal problems. Additionally, the naphthalenedicarboxylic acid produced by the method of the invention contains reduced levels of undesirable impurities and byproducts, and 2,6-naphthalenedicarboxylic acid produced by the method of this invention has a large particle size making filtration and washing of the 2,6-naphthalenedicarboxylic acid more efficient. Importantly, this purification is achieved without first separating the naphthalenedicarboxylic acid from the oxidation reaction mixture. Finally, the method of this invention provides for greater flexibility in the composition of the oxidation reaction mixture and oxidation reaction conditions used for oxidizing the alkyl- or acylaromatic compound to the corresponding aromatic carboxylic acid. For example, oxidation conditions heretofore considered to be undesirable because they result in an excessive amount of trimellitic acid can now be used because the method of this invention provides for the efficient removal of such trimellitic acid before recycling the oxidation reaction mother liquor to the oxidation reaction.

DETAILED DESCRIPTION OF THE INVENTION

Figure 1:
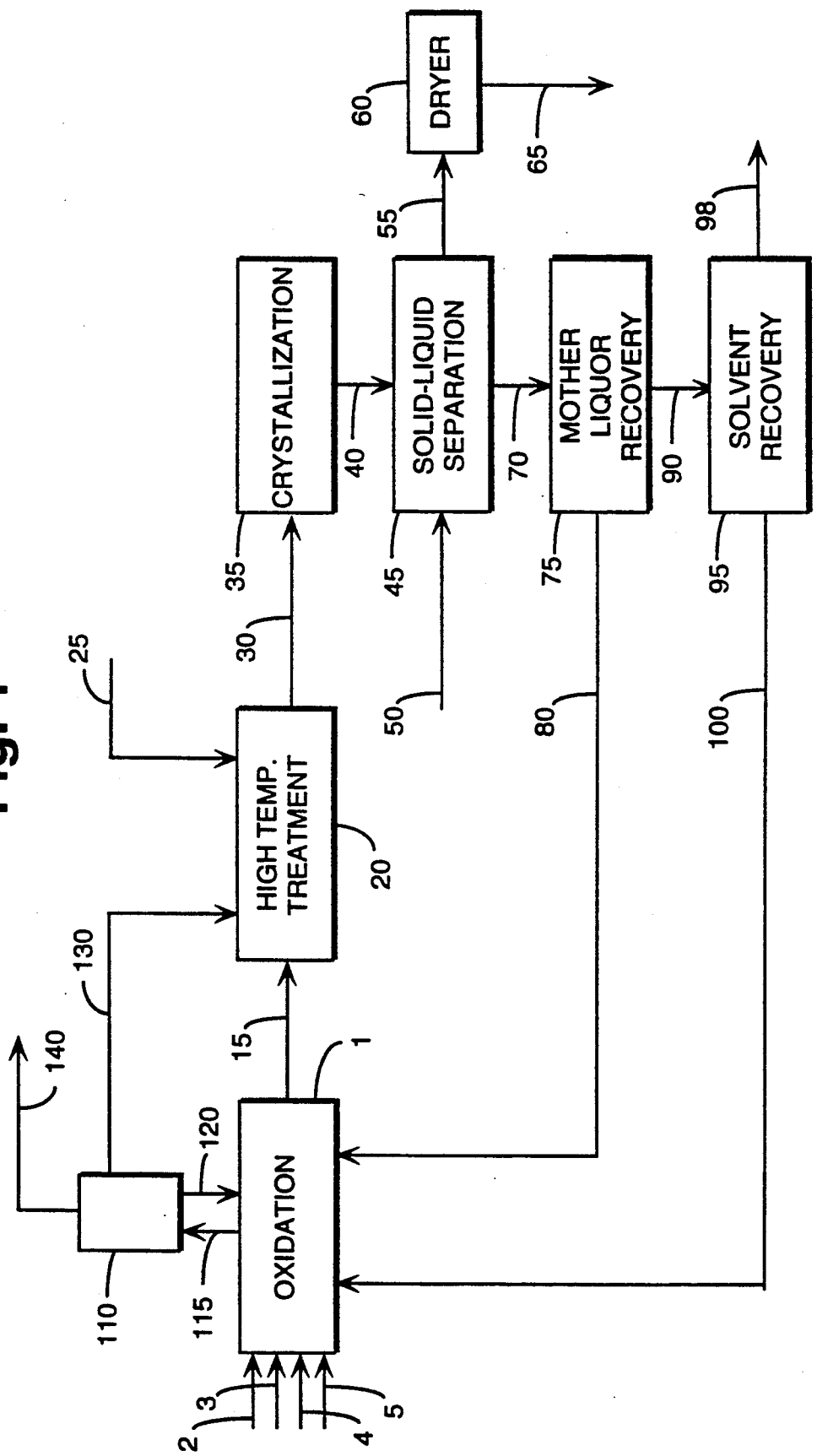
FIG. 1 is a flow-diagram of a preferred embodiment of the present invention showing an integrated method comprising oxidation of 2,6-dimethylnaphthalene, heat treatment of the oxidation reaction mixture, crystallization of 2,6-naphthalenedicarboxylic acid and separation steps.

The oxidation reaction product mixture used in the method of this invention is obtained from the liquid phase, heavy metal catalyzed oxidation of an alkyl- or acyl substituted aromatic compound. Such aromatic compounds include any acyl- and/or alkyl substituted aromatic compound wherein the acyl and/or alkyl group can be oxidized to an aromatic carboxylic acid group. For the purposes of this invention, a formyl group can also be oxidized and is considered to be equivalent to an acyl group. Particularly suitable aromatic feed compounds are those having the structure:

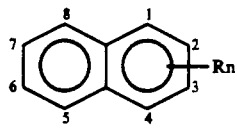

wherein n is an integer from 1 to 8, preferably 1 to 4, more preferably n is 1 or 2, and wherein R is independently selected from the group consisting of alkyl groups having 1 to about 6 carbon atoms, inclusive, and an acyl group containing 1 to about 6 carbon atoms, inclusive. Preferably, R is methyl, ethyl, isopropyl, acetyl, or formyl. Examples of suitable aromatic feed compounds include: o-xylene, m-xylene, p-xylene, 4,4'-dialkyldiphenylether, 3,4'-dialkyldiphenylether, 4,4'-dialkylbiphenyl, 3,3',4,4'-tetraalkyldiphenylether, dixylypropane, 3,3',4,4'-tetraalkyldiphenylsulfone, wherein the alkyl group preferably contains 1 to 4 carbon atoms, inclusive, and more preferably wherein the alkyl group is methyl. Examples of useful naphthalene-based aromatic feed compounds include: 1-methyl- and 2-methylnaphthalene, 1-ethyl-and 2-ethylnaphthalene, 1-isopropyl- and 2-isopropylnaphthalene; and 2,6-dialkyl or 2-acyl-6-alkylnaphthalene compounds such as 2,6-dimethyl-, 2,6-diethyl-, and 2,6-diisopropylnaphthalene; 2-acetyl-6-methylnaphthalene, 2-methyl-6-ethylnaphthalene, 2-methyl-6-isopropylnaphthalene, and the like. Preferred aromatic compounds for the method of this invention are p-xylene, m-xylene and 2,6-dimethylnaphthalene which, when oxidized, are converted to terephthalic acid, isophthalic acid and 2,6-naphthalenedicarboxylic acid, respectively.

Sikkenga et al. U.S. Pat. Nos. 5,034,561; 5,030,781 and 4,950,825 disclose methods for preparing dimethylnaphthalene. In Hagen et al. U.S. Pat. 5,026,917, a process for preparing 2-methyl-6-acetylnaphthalene is disclosed, and in Hagen et al., U.S. Pat. 4,873,386, a process for preparing 2,6-diethylnaphthalene is disclosed.

The most preferred aromatic feed compound for oxidation in the method of this invention is 2,6-dimethylnaphthalene. 2,6-Naphthalenedicarboxylic acid obtained by the oxidation of 2,6-dimethylnaphthalene is a suitable monomer for preparing PEN, a high-performance polyester. Furthermore, 2,6-dimethylnaphthalene is superior to, for example, 2,6-diethyl- or 2,6-diisopropylnaphthalene feed because it is lower in molecular weight and the yield of 2,6-naphthalenedicarboxylic acid per given weight of 2,6-dialkylnaphthalene feed compound is greater for 2,6-dimethylnaphthalene than for 2,6-diethyl- or 2,6-diisopropylnaphthalene.

Methods for conducting the liquid phase, heavy metal catalyzed oxidation of an alkyl- or acyl-substituted aromatic compound to the corresponding aromatic carboxylic acid are well known in the art. For example, U.S. Pats. 4,950,786; 4,933,491; 3,870,754 and 2,833,816 disclose such oxidation methods. In general, suitable heavy metal oxidation catalysts include those metals having an atomic number of about 21 to about 82, inclusive, preferably a mixture of cobalt and manganese. The preferred oxidation solvent is a low molecular weight monocarboxylic acid having 2 to about 6 carbon atoms, inclusive, preferably it is acetic acid or mixtures of acetic acid and water. A reaction temperature of about 300° F. to about 450° F. is typical, and the reaction pressure is such that the reaction mixture is under liquid phase conditions. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of molecular oxygen is also required, and typically it is air.

A particularly suitable method for oxidizing a 2,6-dialkyl or 2-acyl-6-alkylnaphthalene to 2,6-naphthalenedicarboxylic acid is disclosed in U.S. Pat. 4,933,491 to Albertins et al. Suitable solvents for such liquid phase oxidation reaction of 2,6-dialkyl or 2-acyl-6-alkylnaphthalene include benzoic acid, any aliphatic $C_2$–$C_6$ monocarboxylic acid such as acetic acid, propionic acid, n-butyric acid, isobutyric acid, n-valeric acid, trimethylacetic acid, caproic acid, and water. Preferably the solvent is a mixture of water and acetic acid, which mixture is preferably 1 to 20 weight percent water. The source of molecular oxygen employed in such liquid phase oxidation of a 2,6-dialkyl or 2-acyl-6-alkylnaphthalene can vary in molecular oxygen content from that of air to oxygen gas. Because of economy, air is the preferred source of molecular oxygen.

The catalyst employed in such oxidation of a 2,6-dialkyl or 2-acyl-6-alkylnaphthalene comprises a bromine-containing compound and at least one of a cobalt- and manganese-containing compound. Preferably, the catalyst comprises cobalt-, manganese-, and bromine-containing components. The ratio of cobalt (calculated as elemental cobalt) in the cobalt component of the catalyst to 2,6-dialkyl or 2-acyl-6-alkylnaphthalene in the liquid phase oxidation is in the range of about 0.1 to about 100 milligram atoms (mga) per gram mole of 2,6-dialkyl or 2-acyl-6-alkylnaphthalene. The ratio of manganese (calculated as elemental manganese) in the manganese component of the catalyst to cobalt (calculated as elemental cobalt) in the cobalt component of the catalyst in the liquid phase oxidation is in the range of from about 0.1 to about 10 mga per mga of cobalt. The ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine-to-total cobalt and manganese milligram atom ratio is provided by a suitable bromine source such as elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzylbromide, tetrabromoethane, ethylenedibromide, etc.). The total bromine in molecular bromine and ionic bromide is used to determine satisfaction of the elemental bromine-to-total cobalt an manganese milligram atom ratio of 0.1:1.0 to 1.5:1.0. The bromine is released from the organic bromides at the oxidation operating conditions of be readily determined by known analytical means. Tetrabromoethane, for example, at operating temperatures of 335° F. to 440° F. has been found to yield about 3 effective gram atoms of bromine per gram mole.

In operation, the minimum pressure at which the oxidation reactor is maintained is that pressure which will maintain a substantial liquid phase of the 2,6-dialkyl or 2-acyl-6-alkylnaphthalene and at least 70 weight percent of the solvent. The 2,6-dialkyl or 2-acyl-6-alkylnaphthalene and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range within the oxidation reactor is generally from about 250° F., preferably from about 350° F. to about 450° F., preferably to about 420° F. At temperatures greater than 450° F., excessive burning of the solvent and/or naphthalene compound occurs. The solvent residence time in the oxidation reactor is generally from about 20 to about 150 minutes and preferably from about 30 to about 120 minutes.

The oxidation can be performed either in a batch, continuous, or semicontinuous mode. In the batch mode, the 2,6-dialkyl or 2-acyl-6-alkylnaphthalene, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the 2,6-dialkyl or 2-acyl-6-alkylnaphthalene has been completely introduced into the reactor, the temperature of the reactor contents is raised. In the continuous mode, each of the 2,6-dialkyl or 2-acyl-6-alkylnaphthalene, air, solvent, and catalyst are continuously introduced into the oxidation reactor, and a product stream comprising 2,6-naphthalenedicarboxylic acid and catalyst components dissolved in the solvent is withdrawn from the reactor. In the semicontinuous mode, the solvent and catalyst are initially introduced into the reactor and then the 2,6-dialkyl or 2-acyl-6-alkylnaphthalene and air are continuously introduced into the reactor. The hereinabove described method for oxidizing 2,6-dialkyl or 2-acyl-6-alkylnaphthalene compounds can also be used to oxidize other alkyl and/or acyl substituted aromatic compounds such as oxidizing p-xylene to terephthalic acid and m-xylene to isophthalic acid.

For large-scale commercial operation it is preferable to use a continuous oxidation process. In such a process using the preferred 2,6-dimethylnaphthalene as the aromatic feed, the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 370° F. to about 420° F. Acetic acid is the most suitable solvent for such preferred continuous oxidation of 2,6-dimethylnaphthalene.

Depending on the oxidation reaction conditions used, the aromatic feed compound selected, the oxidation catalysts, and the levels of catalyst selected, the reaction mixture produced in the oxidation reaction contains, in addition to the desired aromatic carboxylic acid, a number of impurities and reaction by-products. For example, when 2,6-dimethylnaphthalene is the aromatic feed compound for the oxidation reaction and a catalyst comprising cobalt, manganese and bromine components is used, the oxidation reaction mixture directly from the oxidation reactor, (also called the total reactor effluent or TRE) contains the reaction solvent, which is typically a mixture of acetic acid and water, the desired 2,6-naphthalenedicarboxylic acid, and impurities including trimellitic acid (TMLA), bromo-2,6-naphthalenedicarboxylic acid (BR-2,6-NDA), 2-formyl-6-naphthoic acid (2-FNA), 2-naphthoic acid (2-NA), a collection of other impurities, and cobalt and manganese catalyst components. The acetic acid and water can be removed by evaporation or distillation from the oxidation reaction mixture to leave a residue of solids. Analysis of these solids provides a useful assessment of all of the solid components in the oxidation reaction mixture and consequently an assessment of the yield of desired product and reaction by-products. In a typical oxidation of 2,6-dimethylnaphthalene, the amount of trimellitic acid in the oxidation reaction mixture solids can be as high as 5 wt % of the solids and typically about 3–4 wt. %. The amount of 2-formyl-6-naphthoic acid can be as high as 1 wt % and typically is about 0.4–0.5 wt %. The amount of bromo-2,6-naphthalenedicarboxylic acids can be as high as 3 wt % and is typically about 0.2 to 1 wt %. The total of cobalt and manganese in the solid portion of the oxidation reaction mixture can be as high as 4 wt %. Although the desired 2,6-naphthalenedicarboxylic acid is generally insoluble in the oxidation reaction mixture, particularly when the oxidation reaction mixture is cooled to a temperature below the oxidation reaction temperature, and can be easily separated from the oxidation reaction mixture, the 2,6-naphthalenedicarboxylic acid recovered is also contaminated with trimellitic acid, 2-formyl-6-naphthoic acid, bromo-2,6-naphthalenedicarboxylic acids, other organic impurities and by-products, as well as the cobalt and manganese oxidation metal catalysts. Furthermore, even when the 2,6-naphthalenedicarboxylic acid is separated from the oxidation reaction mixture at an elevated temperature, and even if the separated 2,6-naphthalenedicarboxylic acid is washed with fresh solvent at an elevated temperature to remove residual mother liquor, the recovered 2,6-naphthalenedicarboxylic acid still contains substantial amounts of the aforementioned impurities and by-products which require removal from the 2,6-naphthelenedicarboxylic acid.

However, we have now discovered that the level of the undesirable impurities formed during the liquid phase oxidation of an alkyl- or acyl-substituted aromatic feed compound can be substantially reduced by heating the oxidation reaction product mixture (i.e., the total reactor effluent (TRE)) at an elevated temperature of at least about 500° F., preferably at least about 550° F., and most preferably at least about 600° F. Although reaction temperatures above about 600° F., for example, 650° F., are highly effective, it is preferable not to operate at a temperature greater than 700° F. Importantly, the high temperature step of this invention is subsequent to the oxidation step where, preferably, substantially all of the oxidizable alkyl or acyl groups on the aromatic ring are oxidized to carboxylic acid groups. Additionally, the high temperature step is effective in reducing the level of undesirable impurities in the absence of any added molecular oxygen, i.e., molecular oxygen added from an external source.

While the oxidation reaction product mixture is heat treated at the aforementioned elevated temperatures of at least about 500° F., it is desirable to maintain at least about 50 weight percent and preferably substantially all of the solvent in the liquid phase and to avoid the loss of solvent. Consequently, it is desirable to employ a pressurized vessel to maintain the low molecular weight carboxylic acid oxidation solvent in the liquid phase. A suitable pressure for the heat treatment is a pressure of about 200 psig to about 3000 psig. The pressure required will necessarily be related to the temperature selected and the vapor pressure of water and of the low molecular weight carboxylic acid solvent used for the oxidation reaction. Additionally, the oxidation reaction mixture can be supplemented with additional low molecular weight carboxylic acid, water or other solvent prior to heating to a temperature above about 500° F. Suitable low molecular weight carboxylic acids are those containing 1 to about 8 carbon atoms. Preferably, it is an aliphatic, monocarboxylic acid, and most preferably it is the same low molecular weight carboxylic acid that is used for the oxidation reaction. The amount of solvent present during the heat treating step in the method of this invention can be an amount that provides for the dissolution of substantially all of the aromatic carboxylic acid present. However, complete or substantially complete dissolution is not required. For example, the heat treating step of this invention is effective when at least 10 weight percent, preferably 20 weight percent of the aromatic carboxylic acid is in solution. A suitable weight ratio of solvent to aromatic carboxylic acid is at least about 2:1, preferably from about 3:1 to about 10:1. When the aromatic carboxylic acid is 2,6-naphthalenedicarboxylic acid, the preferred solvent for the high temperature heat treatment is acetic acid, optionally containing about 2 to about 50 weight percent water.

In the heat treatment step of this invention, the oxidation reaction product mixture is heated at a temperature of at least about 500° F. for a time period sufficient to reduce the level of undesirable impurities and by-products contained therein. The time period during which the oxidation reaction mixture is maintained at a temperature of at least about 500° F. is suitably at least about 0.1 minute, preferably at least about 1 minute and most preferably at least about 10 minutes. After this heating at a temperature of at least about 500° F., the levels of undesirable impurities in the oxidation reaction product mixture are reduced. For example, when the oxidation reaction product mixture contains trimellitic acid, the level of trimellitic acid is reduced, when the oxidation reaction mixture contains a formyl naphthoic acid, the level of the formyl naphthoic acid is reduced, and when the oxidation reaction mixture contains one or more bromo naphthalenecarboxylic acids, the level of these brominated acids is reduced. The reduced levels of impurities in the oxidation reaction mixture after the heat treatment according to the method of this invention, for example, provides for a purer form of 2,6-naphthalenedicarboxylic acid when the 2,6-naphthalenedicarboxylic acid is separated from heat-treated the oxidation reaction mother liquor. Additionally, the oxidation reaction mixture mother liquor after the heat treatment according to the method of this invention contains lower levels of trimellitic acid thereby making the mother liquor more suitable for recycle to the oxidation reaction since it contains less trimellitic acid to complex and deactivate the metal oxidation catalysts. For example, when the oxidation reaction mixture is produced by the oxidation of 2,6-dimethylnaphthalene or other 2,6-dialkylnaphthalene compounds and the oxidation reaction mixture contains bromo-2,6-naphthalenedicarboxylic acids, 2-formyl-6-naphthoic acid and trimellitic acid, the amount of bromo-2,6-naphthalenedicarboxylic acid in the oxidation reaction mixture can be reduced by at least about 25 percent and preferably by at least about 50 percent, the amount of 2-formyl-6-naphthoic acid can be reduced by at least about 15 percent, and preferably by at least about 30 percent, and the amount of trimellitic acid can be reduced by at least about 20 percent and preferably by at least about 50 percent. Preferably, the oxidation reaction mixture used in the high temperature treatment step of this invention comprises acetic acid, water, cobalt and manganese oxidation metals, 2,6-naphthalenedicarboxylic acid, trimellitic acid, 2-formyl-6-naphthoic acid and bromo-2,6-naphthalenedicarboxylic acids.

During the heat treating step of the method of this invention, the oxidation reaction mixture containing the aromatic carboxylic acid can be treated with one or more oxidizing, reducing or other purification agents to further improve the purity of the resulting aromatic carboxylic acid and to further eliminate undesirable components such as aldehydes and brominated aromatic compounds in the oxidation reaction mixture mother liquor. For example, the oxidation reaction mixture (either before or after the desired aromatic carboxylic acid is removed) when being heated at a temperature of at least about 500° F. can be treated with one or more oxidizing agents such as manganese dioxide, hypobromous acid, hydrogen peroxide or other peroxides, and the like. Alternatively, and preferably, it can be treated with a reducing agent such as hydrogen gas. Hydrogen gas is the preferred reagent and a suitable hydrogen gas partial pressure is about 5 psig to about 500 psig. When hydrogen gas is used it is also preferable to use one or more standard hydrogenation catalysts. Suitable hydrogenation catalysts include one or more of the Group VIII noble metals. A Group VIII noble metal deposited on a support material is a preferred hydrogenation catalyst. For example, at least one of platinum, palladium, rhodium, rhenium, or ruthenium deposited on a support material such as alumina, titania or carbon. Most preferably, the hydrogenation catalyst is platinum, ruthenium, or palladium deposited on a carbon support. The weight ratio of hydrogenation catalyst to oxidation reaction mixture is suitably about 0.001:1 to about 0.5:1, preferably about 0.005:1 to about 0.05:1, based on the total weight of the catalyst, including the support material, if used. When a Group VIII noble metal catalyst is used the noble metal is present in the catalyst typically in amount of about 0.1 wt % to about 5 wt % based on the total weight of the catalyst. A preferred catalyst is a platinum, ruthenium or palladium on carbon catalyst wherein the metal is present in an amount of about 0.01% to about 1.0 wt % based on the weight of the catalyst.

When hydrogen is used in the heat treatment step of this invention along with a hydrogenation catalyst, it is desirable to operate at a temperature and at a ratio of solvent to aromatic carboxylic acid such that the aromatic carboxylic acid is substantially or, preferably, completely in solution. Under such conditions, it is possible to pass the oxidation reaction mother liquor containing the impure aromatic carboxylic acid through a fixed bed of hydrogenation catalyst. However, when using hydrogen it is not absolutely necessary to have all the aromatic carboxylic acid in solution. For example, the hydrogenation catalyst can be contained on one side of screen or filter or other barrier that permits the passage of dissolved aromatic carboxylic acid, other dissolved components and the hydrogen, but does not permit the passage of particulate material such as the insoluble components of the oxidation reaction mixture, including the aromatic carboxylic acid not in solution. Using this type of arrangement, the hydrogenation reaction can proceed without subjecting the hydrogenation catalyst to the insoluble components of the oxidation reaction mixture, which components could plug the hydrogenation catalyst. However, as mentioned hereinabove, when using hydrogen during the high temperature treatment, it is desirable to operate under conditions where the aromatic carboxylic acid is substantially completely and, preferably, completely in solution. In an integrated process such as in a large scale manufacturing plant, the oxidation reaction mixture exiting the oxidation reaction zone may not contain sufficient low molecular weight carboxylic acid and/or water to dissolve the aromatic carboxylic acid at the temperature used for the high temperature treatment. It may, therefore, be desirable to add additional solvent such as water or a low molecular weight carboxylic acid to the reaction mixture to dissolve additional aromatics, and preferably all, of the aromatic carboxylic acid. One possible source of such solvent is the mixture of low molecular carboxylic acid and water that is obtained from the oxidation reaction mixture vapor which would otherwise be condensed and at least partially returned to the oxidation reaction mixture. However, some or all of this condensate can be added to the high temperature reaction mixture to assist in dissolving the aromatic carboxylic acid. Example 10 hereinbelow provides data for the solubility of 2,6-naphthalenedicarboxylic acid in water and acetic acid. These data can be used to estimate the amount of acetic acid, a preferred solvent, and/or water, another preferred solvent, required to dissolve 2,6-naphthalenedicarboxylic acid at a given reaction temperature.

When hydrogen gas is used in the high temperature process of this invention, the removal of 2-formyl-6-naphthoic acid and bromo-2,6-naphthalenedicarboxylic acid from an oxidation reaction mixture and from the 2,6-naphthalenedicarboxylic acid isolated from the oxidation reaction mixture is facilitated. For example, when hydrogen gas and a suitable hydrogenation catalyst is used during the heat treatment of the oxidation reaction mixture formed by the oxidation of 2,6-dimethylnaphthalene, the hydrogen assists in the removal of 2-formyl-6-naphthoic acid, and the hydrogen also assists in the removal of bromo-2,6-naphthalenedicarboxylic acid. Significantly, the 2-formyl-6-naphthoic acid is converted to materials that when recycled to the oxidation reaction are converted to 2,6-naphthalenedicarboxylic acid. The reaction of bromo-2,6-naphthalenedicarboxylic acid with hydrogen produces 2,6-naphthalenedicarboxylic acid. Thus, there is no loss of valuable product. Consequently, when hydrogen is used during the high temperature treatment, an oxidation reaction mixture containing greater amounts of 2-formyl-6-naphthoic acid and bromo-2,6-naphthalenedicarboxylic acid can be tolerated. Therefore, the conditions used to oxidize the 2,6-dialkyl- or 2-alkyl-6-acylnaphthalene compound can be adjusted to provide for higher levels of 2-formyl-6-naphthoic acid and/or bromo-2,6-naphthalene-dicarboxylic acid. This is advantageous because in prior art processes it was necessary to use rather severe oxidation conditions to assure the complete oxidation of the 2-formyl-6-naphthoic acid to 2,6-naphthalanedicarboxylic acid. However, the severe oxidation conditions that provide for low levels of 2-formyl-6-naphthoic acid also produces greater amounts of trimellitic acid. Therefore, the method of this invention, wherein hydrogen is added during the high temperature treatment, provides for the flexibility of selecting oxidation conditions that produces aromatic aldehydes and brominated aromatic compounds because the treatment with hydrogen facilitates the removal of such compounds from the oxidation reaction mixture.

Following the high temperature treatment step in the method of this invention, either with or without the use of hydrogen or other purification agent, the mixture is typically cooled to promote the crystallization of the desired aromatic carboxylic acid. The degree of cooling necessary will depend on such variables as the specific aromatic carboxylic acid present, the amount of low molecular weight carboxylic acid solvent used, the temperature used for the high temperature treatment, and the desired purity of the aromatic carboxylic acid.

However, in general, the reaction mixture is cooled to a temperature of no more than about 450° F., preferably in the range of about 100° F. to about 400° F., more preferably about 150° F. to about 350° F. When the aromatic carboxylic acid is 2,6-naphthalenedicarboxylic acid, the reaction mixture is preferably cooled to a temperature less than about 500° F., more preferably in the range of about 200° F. to about 450° F.

While the reaction mixture can be cooled relatively rapidly by using, for example, one or more flash crystallizers, slow cooling is preferred. Slow cooling provides for larger particle size product and may provide for purer aromatic carboxylic acid. Preferably, the cooling rate is no more than about 80° F./minute, more preferably no more than about 50° F./minute. Most preferably the cooling rate is in the range of about 1° F./minute to about 40° F./minute.

An advantage of the high temperature treatment step in the method of this invention is the formation of large particle size aromatic carboxylic acid. For example, the 2,6-naphthalenedicarboxylic acid isolated directly from the oxidation reaction mixture without a high temperature treatment typically has a small mean particle size of about 15-20 microns, as measured by a Microtrac® particle size analyzer, and also contains a substantial amount of very fine particles, e.g., about 20-40 wt. % of the particles have a particle size less than about 11 microns. The method of this invention, however, produces 2,6-naphthalenedicarboxylic acid having a mean particle size of at least about 40 microns, more preferably at least about 60 microns, and, significantly, only a small percentage of the 2,6-naphthalenedicarboxylic acid is in the form of very small particle, e.g., no more than about 15 wt. % of the 2,6-naphthalenedicarboxylic acid having a particle size less than about 11 microns and, more preferably, no more than about 10%. 2,6-Naphthalenedicarboxylic acid having a mean particle size of 100 microns and greater have been prepared by the method of this invention.

The formation of large particle size aromatic carboxylic acid, and particularly 2,6-naphthalenedicarboxylic acid, is desirable because the large particle size aromatic carboxylic acid is more easily filtered or otherwise separated from the reaction mixture mother liquor, and is also more easily washed with solvent to remove the last traces of mother liquor. Additionally, the presence of the very fine particles of aromatic carboxylic acid causes plugging of filters and other devices used to separate the aromatic carboxylic acid from the reaction mother liquor or wash solvent.

After the heat treatment step in the method of this invention, either with or without a cooling step, the solid aromatic carboxylic acid, and preferably 2,6-naphthalenedicarboxylic acid, is partitioned, i.e., separated, from the reaction mother liquor. Any suitable means can be used for this partitioning step, such as filtration, centrifugation, settling and the like. The mother liquor separated from the aromatic carboxylic acid contains valuable oxidation catalyst metals and, as discussed hereinabove, is typically recycled at least in part to the oxidation reaction mixture. Some or all of the low molecular weight carboxylic acid solvent can be removed prior to recycle. The aromatic carboxylic acid collected in the apparatus used for partitioning the aromatic carboxylic acid from the high temperature reaction mixture is optionally washed with a solvent to remove residual mother liquor. This solvent can be water, a low molecular weight carboxylic acid having 1 to about 6 carbon atoms, preferably acetic acid, mixtures of such low molecular weight carboxylic acid with water, or any other suitable solvent such as toluene, xylene, a $C_9$ aromatic, and the like. The weight ratio of wash solvent to aromatic carboxylic acid is suitably about 0.2:1 to about 3:1. When the aromatic carboxylic acid is 2,6-naphthalenedicarboxylic acid, the preferred wash solvent is acetic acid or mixtures of acetic acid and water, where the water present is about 5 to about 95 weight percent of the mixture, and wherein the weight ratio of acetic acid or mixture of acetic acid and water to 2,6-naphthalenedicarboxylic acid is about 0.2:1 to about 2:1. Furthermore, it is preferable that the wash solvent be at an elevated temperature preferably at about 200° F. to about 450° F. Although one wash step is usually sufficient, additional washing steps can be used.

After the aromatic carboxylic acid is partitioned from the high temperature reaction mixture, or after the optional washing step, the aromatic carboxylic acid is typically dried to remove the remaining solvent. The dried aromatic carboxylic acid is used as is for one or more of the heretofore mentioned applications, or it is purified further by one or more purification procedures such as the esterification procedure described below. For example, when the aromatic carboxylic acid is 2,6-naphthalenedicarboxylic acid, it can be purified by heating it with a solvent comprising a mixture of water and acetic acid at a temperature of at least about 500° F. in the presence of hydrogen and a Group VIII noble metal hydrogenation catalyst.

As mentioned hereinabove, the aromatic carboxylic acid recovered from the oxidation reaction mixture after the oxidation reaction mixture is heated at elevated temperatures according to the method of this invention can be purified further by converting the aromatic carboxylic acid to an ester. The ester can be purified by methods such as recrystallization, distillation, sublimation, etc. The esters are suitably prepared by methods well known in the art. For example, the aromatic carboxylic acid can be heated at an elevated temperature in the presence of an alcohol, and, optionally, in the presence of one or more esterification catalysts. Typically, the alcohol selected is a low-molecular weight alcohol having 1 to about 6 carbon atoms. Methods for preparing the ester of 2,6-naphthalenedicarboxylic acid are disclosed in U.S. Pat. No. 4,886,901 to Holzhauer et al., and in U.S. patent applications 07/708,492 and 07/708,500 filed on May 31, 1991, the specifications of such patent and applications are hereby incorporated by reference.

An advantage of the present invention is that the aromatic carboxylic acid prepared according to the method of this invention is more suitable for preparing an ester. This is because the aromatic carboxylic acids are purer than they would otherwise be and during the preparation and purification of the ester, the purer form of aromatic carboxylic acid contributes less impurities that need to be removed during the ester purification process. For example, a preferred method for preparing the dialkylester of 2,6-naphthalenedicarboxylic acid is to react 2,6-naphthalenedicarboxylic acid with a molar excess of an alcohol, preferably methanol, at an elevated temperature. For example, a weight ratio of alcohol to 2,6-naphthalenedicarboxylic of about 1:1 to about 10:1, respectively, at a temperature in the range of about 100° F. to about 700° F. An esterification catalyst such as sulfuric acid, phosphoric acid, hydrochloric acid or other strong acid, in an amount of about 0.1 to about 10 weight percent based on the weight of the 2,6-naphthalenedicarboxylic acid, or one or more of the metal-based catalysts disclosed in British Patent Specification 1,437,897 may be used, if desired. Following the esterification reaction, the mixture is cooled to crystallize the product ester. The product ester is preferably recrystallized in methanol or an aromatic solvent such as toluene, or a xylene, and the recrystallized product is optionally fractionally distilled at reduced pressure, preferably in a high efficiency fractionation column, to form a purified dimethyl-2,6-naphthalenedicarboxylate. During the preparation and purification of this as with other aromatic carboxylic acid esters, a number of process streams containing concentrates of impurities are produced. For example, when the ester is crystallized, the mother liquor from the esterification reaction contains impurities such as fully or partially esterified oxidation impurities. This stream, after removal of substantially all of the alcohol, can be recycled to the oxidation reaction mixture or, preferably, it can be recycled to the high temperature heating step of this invention. Similarly, the mother liquor from the recrystallization reaction, after removal of substantially all of the methanol or aromatic solvent, can be recycled to the oxidation reaction mixture or, preferably, to the high temperature heating step of this invention. Also, if a distillation of the ester is performed, the distillation bottoms contain a concentration of one or more impurities and the distillation bottoms, or a part thereof, can be recycled to the oxidation reaction mixture or, preferably, to the high temperature heating step of this invention.

Although it is preferable to perform the heat treatment step of this invention prior to separating the aromatic carboxylic acid from the oxidation reaction mixture, heat treating the mother liquor after the separation is also beneficial. Thus, another embodiment of the method of this invention is to first separate the aromatic carboxylic acid from the oxidation reaction mixture, and subsequently subject the recovered mother liquor to the high temperature treatment as described hereinabove.

The high temperature heat treatment step of this invention can be conducted in the batch mode as well as a continuous mode of operation.

DETAILED DESCRIPTION OF THE FIGURE

FIG. 1 is a schematic of the preferred method of operating this invention using 2,6-dimethylnaphthalene as the feed for the oxidation reaction. The liquid phase, catalytic oxidation of 2,6-dimethylnaphthalene occurs in reactor section 1. Feed lines 2-5 are used to feed, respectively, 2,6-dimethylnaphthalene, acetic acid oxidation solvent, catalyst (i.e., bromine, cobalt and manganese components) and air, to the oxidation reactor. The total oxidation reactor effluent (i.e., impure 2,6-naphthalenedicarboxylic acid, water, and the acetic acid reaction solvent containing dissolved catalyst components and reaction by-products and impurities) is fed to the high temperature treatment reactor 20 through line 15. In the high temperature treatment reactor, the total oxidation reactor effluent is heated to an elevated temperature of at least about 500° F. to reduce the levels of impurities and byproducts in the mother liquor, to improve the purity of the 2,6-naphthalenedicarboxylic acid and to increase the particle size of the 2,6-naphthalenedicarboxylic acid. This reactor can be for example, a stirred tank reactor or a compartmentalized reactor. Optionally, hydrogen gas can be added to the high temperature reactor through line 25 and a suitable hydrogenation catalyst can be added to the high temperature reactor 20. The product mixture from the high temperature reactor is cooled in crystallizer 35. Cooling is suitably accomplished by a pressure reduction allowing the mixture to cool by the evaporation of solvent as the pressure is reduced. If a more gradual cooling is desired, a series of crystallizers can be used in order to reduce the temperature in a stepwise manner. Alternatively, a scraped-wall tubular heat exchanger can be used to gradually cool the mixture. Gradual cooling promotes the formation of large crystals of 2,6-naphthalenedicarboxylic acid. After crystallization, the crystallized 2,6-naphthalenedicarboxylic acid and the mother liquor are transferred through line 40 to a solid-liquid separation device 45. The solid liquid separation device is suitably a rotary filter, centrifuge or settling vessel. The collected 2,6-naphthalenedicarboxylic acid is optionally washed with, for example, acetic acid or a mixture of acetic acid and water. The wash liquid, optionally at an elevated temperature, is added to the solid-liquid separation device through line 50. Solid, wet 2,6-naphthalenedicarboxylic acid is sent through line 55 to dryer 60 where any residual solvent is evaporated. The product 2,6-naphthalenedicarboxylic acid exits dryer through line 65. The liquid separated from the reaction mixture in the solid-liquid separating device, as well as the used wash solvent, is sent to a mother liquor recovery unit 75 through line 70. A portion of the mother liquor, optionally having at least some of the water removed, is recycled to the oxidation reactor through line 80. The remaining portion, for example, 5 to 50 percent of the total mother liquor, is sent to the solvent recovery unit 95 through line 90. The solvent recovery unit is typically a multi-step distillation apparatus for removing water from the acetic acid solvent. The recovered acetic acid is optionally recycled to the oxidation reactor 1, bottoms from the solvent recovery are purged through line 98. During the oxidation reaction, an overhead condenser 110 condenses and cools the acetic acid/water mixture vapor produced by the exothermic oxidation reaction and supplied to the condenser through line 115. The cool condensate is, in part, returned to the reactor through line 120 to control the temperature of the oxidation reaction. A portion of the condensate, which is enriched in water relative to the oxidation solvent mixture is also sent to the high temperature treatment reactor 20 through line 130. The proportion of condensate returned to the reactor compared to that sent to the high temperature reactor depends on the level of solvent desired in the high temperature reactor. The ability to add the oxidation reaction condensate to the high temperature reactor provides for the ability to provide for lower levels of water in the oxidation reactor. Lower water levels in the oxidation of 2,6-dimethylnaphthalene to 2,6-naphthalenedicarboxylic acid provides for reduced levels of oxidation impurities and by-products.

The present invention will be more clearly understood from the following examples. It being understood, however, that these examples are presented only to illustrate some embodiments of the invention and are not intended to limit the scope thereof.

EXAMPLES

The following is the general oxidation procedure that was used to oxidize 2,6-dimethylnaphthalene to 2,6-naphthalenedicarboxylic acid for Examples 1 and 2.

The oxidation apparatus consisted of a one-liter titanium reactor equipped with an overhead, water-cooled titanium condenser, a thermowell, an inlet line for air, a heated feed line, and a pressure regulator. Acetic acid was used as the oxidation solvent and cobalt (II) acetate tetrahydrate and manganese (II) acetate tetrahydrate were used as the oxidation catalysts. Aqueous hydrobromic acid was the source of bromine for the oxidation reaction. The condenser provided for cooling by returning to the reactor condensed solvent that vaporized by the heat generated in the oxidation reaction. During the oxidation reaction, both air and the 2,6-dimethylnaphthalene feedstock were fed to the oxidation reactor so that there was a slight excess of air and to provide up to 6% oxygen in the vent gas. At the end of the oxidation reaction, the feedstock and air flow into the reactor were stopped and the reactor contents, i.e., the total reactor effluent, were transferred to a product receiver through a transfer line. The total reactor effluent was allowed to cool in the product receiver to below the boiling point of acetic acid at ambient pressure.

Particle size was measured using a Microtrac II ™ Standard Range Analyzer manufactured by Leeds and Northrup Co., St. Petersburg, Fla. Methanol (or water) was used as circulating liquid for suspending the 2,6-naphthalenedicarboxylic acid particles. This method is a based on laser light scattering, and provides both a mean (average) and median value for the particles measured. The weight percent of the 2,6-naphthalenedicarboxylic acid having a particle size of less than 11 microns can also be determined by this particle size analysis. Organic components were analyzed by liquid chromatography. Metals and bromine were measured by X-ray fluorescence spectroscopy.

In the following Examples and Tables, 2,6-naphthalenedicarboxylic acid is 2,6-NDA, trimellitic acid is TMLA, 2-formyl-6-naphthoic acid is 2-FNA, 2-naphthoic acid is 2-NA, and bromo-2,6-naphthalenedicarboxylic acid is Br-2,6-NDA.

Values in the Tables and Examples referred to as "Normalized 2,6-NDA", were obtained by dividing the actual percent 2,6-NDA obtained directly from the liquid chromatographic analysis by the "Total" value reported and multiplying by 100. Because of the magnitude of signal for the 2,6-NDA component, the actual value obtained is a less accurate measurement of concentration. The value was, therefore, normalized as described above. Values of 0.00 in the Tables indicate that the component was not detected by the analysis method used.

EXAMPLE 1

Table I reports the data for five oxidation reactions each using the same weight ratio of oxidation solvent to 2,6-dimethylnaphthalene feedstock. For Runs 1 and 3, oxidation conditions were selected to minimize the amount of 2-formyl-6-naphthoic acid in the product. This would be desirable in a conventional process because 2-FNA is difficult to remove and it is an undesirable component in 2,6-NDA used for preparing PEN and other polyesters. However, as demonstrated by the data in Table 1, the conditions that minimize 2-FNA also cause the formation of trimellitic acid and increased burning of the acetic acid solvent as evidenced by the high amount of carbon oxides. For Runs 2, 4 and 5, conditions were selected so that the amount of TMLA and/or carbon oxides were reduced to produce, generally, a higher yield of 2,6-NDA but also a higher yield of the undesirable 2-FNA.

However, as discussed hereinabove and demonstrated in subsequent Examples, the high temperature heating method of this invention can be used to reduce the level of 2-FNA in the oxidation reaction mixture. Additionally, when hydrogen is employed in this heating step, the 2-FNA is presumably converted to an intermediate that, when recycled to the oxidation reaction mixture, is oxidized to 2,6-naphthalenedicarboxylic acid.

EXAMPLE 2

Table 2, Runs 1-3, reports data for the oxidation of 2,6-dimethylnaphthalene to 2,6-naphthalenedicarboxylic acid using reactions conducted at decreasing weight ratios of solvent to 2,6-dimethylnaphthalene feedstock. Low ratios of solvent to feedstock are desirable because more 2,6-NDA can be prepared per given size oxidation reactor, and these data demonstrate that low ratios of solvent-to-feedstock can successfully be used. Furthermore, the amount of reaction byproduct such as bromo-2,6-naphthalenedicarboxylic acid caused by the lower ratio of solvent to 2,6-dimethylnaphthalene feedstock can be reduced, and in some cases its presence can be eliminated using the method of this invention. Therefore, the method of this invention allows for the use of lower amounts of solvent in the oxidation reaction mixture.

Table 2, Runs 4-6, demonstrate that the use of higher levels of bromine in the oxidation reaction can cause a desirable decrease in the amount of acetic acid burning as identified by the carbon oxide production. However, the increase in bromine in the oxidation reaction mixture increases the amount of bromo-2,6-naphthalenedicarboxylic acids produced. However, as described hereinabove and as demonstrated subsequently, the method of this invention can be used to decrease the level of Br-2,6-NDA in the oxidation reaction product mixture. Also, when hydrogen is used, the bromo-2,6-naphthalenedicarboxylic acid is converted to 2,6-naphthalenedicarboxylic acid.

The following Examples 3-4 demonstrate the high temperature treatment of this invention. These Examples were conducted using crude 2,6-naphthalenedicarboxylic acid made in a continuous, liquid phase oxidation process using acetic acid as a solvent and catalyzed by cobalt, manganese and bromine. This 2,6-naphthalenedicarboxylic acid contains most of the impurities and by-products expected to be found in an actual oxidation reaction effluent, but in somewhat lower concentrations.

EXAMPLE 3

Table III, Runs 1-6, were conducted in a 50 ml high pressure reactor fitted with an internal thermocouple and charged with the indicated solvents and crude 2,6-NDA having the composition listed in Table III. A wire mesh basket containing the catalyst as 0.5% Pd/carbon granules was inserted into the reactor. The catalyst had been previously heated in the solvent for 72 hours at 530° F. to "age" it and impart more stability to the catalyst. Finally, the reactor was purged with hydrogen to remove the oxygen and pressurized with the indicated amount of hydrogen and sealed.

The reactor was placed in a shaker device which agitated the reactor contents by shaking at 360 cycles/minute. While shaking, the reactor was partially immersed into a sand bath to attain the desired temperature as measured by the internal thermocouple. The shaking and reaction temperature was maintained for 30 minutes as indicated in Table III. After the reaction period, the reactor was withdrawn from the sand bath, cooled to room temperature, weighed to determine reactor integrity, and the entire reactor contents transferred to a dish for drying in a vacuum oven at 175°–195° F. The dry total product was mixed well for uniformity of sampling and analyzed.

Runs 1-3 in Table III were conducted with 85% acetic acid and 15% water using various hydrogen pressures. This solvent ratio is similar to that expected in the oxidation reactor effluent. In all cases, 100% of the Br-2,6-NDA was converted, 62–72% of the TMLA, and 61–71% of the 2-FNA. The amount of 2-NA formed by decarboxylation of 2,6-NDA ranged from 0.0 to 0.06 weight percent. The amount of dicarboxytetralin increased with increasing hydrogen pressure and ranged from 0.02 to 0.14%. Thus, high conversion of impurities was obtained along with low formation of by-products. The net increase in the normalized % 2,6-NDA indicates that some of the impurities (like Br-2,6-NDA) are being converted to 2,6-NDA.

In Runs 4-6, a 50/50 mixture of acetic acid/water was used. The conversion of Br-2,6-NDA was 100% just as with the 85% acetic acid. The conversion of TMLA and 2-FNA was somewhat higher than with the 85% acetic acid. However, the amount of 2-NA and tetralin formed was greater than with the 85% acetic acid.

EXAMPLE 4

This run was made in a large, stirred, high-pressure reactor which was charged with the crude 2,6-NDA feedstock, 90% acetic acid/water, hydrogen and hydrogenation catalyst. Following the reaction period, the run was cooled to 300° F. and filtered via a screen in the bottom of the reactor. The reactor containing the cake was then washed at 300° F. with an additional 400 g of 90% acetic acid/water and the mother liquor removed by filtration was added to the first mother liquor. The results are reported in Table IV.

The mother liquor and cake were both dried in a vacuum oven at 175°–195° F., mixed for uniformity and analyzed by liquid chromatography for organic composition and by x-ray fluorescence spectroscopy for metals. The cake samples were analyzed by a Microtrak ™ particle analyzer for particle size. The weights and compositions of the filtrate and cake were used to calculate the total product composition which is reported in Table IV as the "Combined Products."

The cake composition indicates that a high purity 2,6-NDA product can be obtained by using the hydrogen/Pd/carbon treatment followed by conventional solid/liquid separation techniques. The "Combined Products" data indicates that there was an actual conversion of the TMLA, Br-2,6-NDA, and 2-FNA to other products allowing their removal from the cake. The composition of the filtrate indicates that the bulk of the metals and bromine are concentrated there for recycle to the oxidation reactor. In addition, the TMLA concentration in this stream is low due to conversion to TA and IA (included in "Others"). The particle size of the purified cake is much larger than that of the 2,6-NDA feedstock and contains fewer fines indicating that the purification process will make solid recovery easier.

EXAMPLE 5

To prove that the treatment of Br-2,6-NDA with hydrogen and Pd/carbon will result in the formation of 2,6-NDA, a run conducted with a feedstock comprised of high purity 2,6-NDA spiked with 4.3% Br-2,6-NDA (about 2-10 times higher than normally obtained). After treatment for 10 minutes at 600° F., the total reaction mixture was dried and the dried product contained only 0.02% Br-2,6-NDA and the normalized 2,6-NDA content increased by 4.8% indicating a good balance between Br-2,6NDA loss and 2,6-NDA appearance. No other major new components were detected in the product. This example supports the stated advantage of this invention as a method to sncrease 2,6-NDA yield while allowing greater flexibility in the oxidation step. The results are reported in Table V.

EXAMPLE 6

For this example, a total oxidation reactor effluent (TRE) obtained from a continuous oxidation reaction was used after cooling but without any separation, concentration, or dilution of the total oxidation reactor effluent. This TRE contained acetic acid/water as solvent and a solids content of about 25 wt. %. A sample of this TRE was dried in a vacuum oven and the solids had the composition indicated in Table VI. The TRE was charged to a 300 ml autoclave along with 0.5% Pd/carbon catalyst in a stainless steel basket. The autoclave was purged of oxygen with helium then pressurized to 300 psig with hydrogen. With stirring, the autoclave was heated rapidly to the indicated temperature and held at that temperature for the indicated time. At the end of the reaction period, the heating was stopped and the autoclave was allowed to cool to 400° F. for about 30 minutes, then cooled rapidly to room temperature. The entire reactor contents were removed, the solvent evaporated in a vacuum oven at 185° F., and the mixed solids analyzed by liquid chromatography.

Run 1 at 600° F. illustrates that high conversions of TMLA, Br-2,6-NDA and 2-FNA can be obtained in a short reaction time of 10 minutes at 600° F. using a fresh hydrogenation catalyst. This is true in spite of the high concentration of solids (25%) which might have prevented complete dissolution of all solids at one time. The crystallized product has a large mean particle size with few fines. Less than 20% of the bromine was lost as HBr although 90% of the Br-2,6-NDA was converted. No 2-NA formation by decarboxylation was detected.

Run 2 was conducted at a lower temperature with a used catalyst and a longer reaction time. The results are similar to those in Run 1 with high TMLA and Br-2,6-NDA conversion but somewhat lower levels of 2-FNA conversion. There was lower bromine loss at the lower temperature.

Operation at the lower temperature reduces reactor pressure and corrosion rates. However, complete dissolution of the solids was probably not obtained. For use in a fixed bed reactor, complete dissolution may be necessary to prevent plugging of the catalyst bed.

In the following Examples 7-9, the same reactor was used as in Example 3, and the total reactor effluent (TRE) used in all of these Examples was obtained from the continuous oxidation of 2,6-dimethylnaphthalene to 2,6-naphthalenedicarboxylic acid in acetic acid/water solvent catalyzed by cobalt, manganese and bromine.

EXAMPLE 7

Table VII provides the results from heating the TRE at a temperature ranging from 575°–650° F. for either 10 or 30 minutes, as indicated for Runs 1-6. Hydrogen was not used. The total reactor product was dried to remove the solvent and analyzed. The results indicate that trimellitic acid (TMLA) is largely converted to terephthalic acid (TA) and isophthalic acid (IA). In addition, the Br-2,6-NDA is converted and a large percentage of the 2-FNA is converted by the high temperature treatment.

EXAMPLE 8

Table VIII reports data for a series of high temperature treatment procedures without hydrogen wherein a hot filtration was used and the product filter cake was washed at 200° F. with a mixture of 85% acetic acid and 15% water. These data demonstrate, that under a variety of conditions, the 2,6-naphthalenedicarboxylic acid produced by the method of this invention is greatly reduced in metals, TMLA, bromine and several of the organic impurities. Significantly, the particle size of the 2,6-naphthalenedicarboxylic acid produced was considerably larger than the particle size of the 2,6-naphthalenedicarboxylic acid in the TRE starting material.

EXAMPLE 9

Table IX reports data for the results for the high temperature treatment according to the method of this invention wherein after the high temperature treatment the product 2,6-naphthalenedicarboxylic acid was filtered hot from the reactor, but no washing procedure was used. These data also demonstrate that the high temperature treatment facilitates removal of TMLA, Br-2,6-NDA and 2-FNA from the final product. Significantly, the "dry filtrate" which contains the bulk of the oxidation reaction catalyst metals contains low levels of TMLA which means that this material can be recycled to the oxidation reaction without adding undesirable TMLA.

EXAMPLE 10

Solubility data for 2,6-naphthalenedicarboxylic acid in distilled water and in acetic acid are provided below.

| Temperature (°C./°F.) | Solubility (grams 2,6-NDA/100 g solvent) | | |
|---|---|---|---|
| | Water | Acetic Acid | Acetic Acid/Water* |
| 160/320 | 0.041 | 0.16 | 0.18 |
| 200/392 | 0.22 | 0.44 | 0.59 |
| 240/464 | 1.19 | 1.2 | 2.0 |
| 280/536 | 6.07 | 3.1 | 4.5 |
| 320/608 | 33.2 | — | 10.8 |

*85 wt. % acetic acid

TABLE I

| | Run # | | | | |
|---|---|---|---|---|---|
| | 1 | 2 | 3 | 4 | 5 |
| Reaction Conditions | | | | | |
| Temperature (°F.) | 415 | 385 | 410 | 410 | 410 |
| Co:Mn:Br Atom Ratio | 2:1:3.3 | 1:3:2 | 3:1:2 | 1:3:2 | 1:3:2 |
| Co (wt %)[a] | 0.15 | 0.15 | 0.15 | 0.15 | 0.15 |
| Residence Time, minutes | 44 | 112 | 71 | 44 | 110 |
| Water (wt %)[a] | 5 | 4 | 5 | 25 | 5 |
| Solvent/2,6-DMN (wt)[b] | 6 | 6 | 6 | 6 | 6 |
| Reactor Yields (mole %) | | | | | |
| 2,6-NDA | 88 | 92 | 85 | 86 | 90 |
| TMLA | 4.6 | 2.4 | 4.5 | 5.5 | 3.8 |
| Carbon Oxides | 8 | 6 | 11 | 2.6 | 9.1 |
| 2-FNA | 0.09 | 0.41 | <0.1 | 0.30 | 0.30 |

[a] Weight percent based on total solvent weight.
[b] Weight ratio of total solvent to 2,6-dimethylnaphthalene feed.

TABLE II

| | Run # | | | | | |
|---|---|---|---|---|---|---|
| | 1 | 2 | 3 | 4 | 5 | 6 |
| Reaction Conditions | | | | | | |
| Temperature (°F.) | 390 | 390 | 400 | 400 | 410 | 400 |
| Co:Mn:Br Atom Ratio | 1:3:2 | 1:3:2 | 1:3:2 | 1:3:2 | 1:3:2 | 1:3:3 |
| Co (wt %)[a] | 0.10 | 0.125 | 0.125 | 0.125 | 0.125 | 0.125 |
| Residence Time, minutes | 50 | 64 | 57 | 59 | 57 | 56 |
| Water (wt %)[a] | 5 | 5 | 5 | 10 | 10 | 10 |
| Solvent/2,6-DMN (wt %)[b] | 6 | 5 | 4 | 4 | 4 | 4 |
| Reactor Yields (mole %) | | | | | | |
| 2,6-NDA | 91 | 91 | 91 | 89 | 89 | 86 |
| TMLA | 4.2 | 4.1 | 3.4 | 4.0 | 4.1 | 3.8 |
| Carbon Oxides | 3.0 | 2.7 | 3.8 | 3.1 | 3.1 | 2.1 |
| 2-FNA | 0.52 | 0.58 | 0.42 | 0.55 | 0.37 | 0.53 |
| Br-2,6-NDA | 0.12 | 0.14 | 0.23 | 0.47 | 0.43 | 0.92 |

[a] Weight percent based on total solvent weight.
[b] Weight ratio of total solvent to 2,6-dimethylnaphthalene feed.

TABLE III

| | 2,6-NDA Feed[a] | Run # | | | | | |
|---|---|---|---|---|---|---|---|
| | | 1 | 2 | 3 | 4 | 5 | 6 |
| Reactor Charge | | | | | | | |
| 2,6-NDA (g) | | 4.00 | 4.01 | 4.00 | 4.00 | 4.00 | 4.00 |
| Solvent Used (wt. % Acetic Acid/wt. % Water) | | 85/15 | 85/15 | 85/15 | 50/50 | 50/50 | 50/50 |
| Solvent Wt. (g) | | 20.0 | 20.0 | 20.0 | 20.0 | 20.0 | 20.0 |
| Catalyst Used[b] | | 0.5 wt. % Pd/C | 0.5 wt. % Pd/C | 0.5 wt. % Pd/C | 0.5 wt. % Pd/C | 0.5 wt. % Pd/C | 0.5 wt. % Pd/C |
| Catalyst Wt. (g) | | 0.43 | 0.43 | 0.43 | 0.42 | 0.42 | 0.42 |
| Catalyst Previous Uses | | 2 | 0 | 1 | 2 | 0 | 1 |
| Conditions | | | | | | | |
| Temperature (°F.) | | 600 | 600 | 600 | 600 | 600 | 600 |
| Time from 100° F. to Reaction | | 2:05 | 2:10 | 2:30 | 1:50 | 1:50 | 2:00 |

TABLE III-continued

| | 2,6-NDA Feed[a] | Run # 1 | 2 | 3 | 4 | 5 | 6 |
|---|---|---|---|---|---|---|---|
| Temp. (min.) | | | | | | | |
| Reaction Time (min.) | | 30 | 30 | 30 | 30 | 30 | 30 |
| Shaking Speed (cpm) | | 360 | 360 | 360 | 360 | 360 | 360 |
| Hydrogen Pressure at 70° F. (psig) | | 15 | 30 | 100 | 15 | 30 | 100 |
| Product Weight (g)[c] | | 24.20 | 24.29 | 24.26 | 23.96 | 24.17 | 24.19 |
| Wt. % Reactor Loss (g) | | 3.20 | 2.84 | 2.96 | 4.16 | 3.32 | 3.24 |
| Dry Down Weight (g) | | 3.98 | 3.94 | 3.95 | 4.00 | 3.99 | 3.93 |
| Product Analysis (Wt. %) | | | | | | | |
| 2,6-NDA | 90.06 | 91.98 | 88.01 | 89.21 | 92.64 | 89.24 | 89.45 |
| 2,7-NDA | 0.01 | 0.00 | 0.01 | 0.01 | 0.00 | 0.01 | 0.01 |
| TMLA | 2.19 | 0.60 | 0.70 | 0.82 | 0.15 | 0.33 | 0.60 |
| $C_8$ Acids | 0.02 | 1.15 | 0.98 | 0.79 | 1.35 | 1.31 | 1.16 |
| Br-2,6-NDA | 0.59 | 0.00 | 0.00 | 0.00 | 0.00 | 0.00 | 0.00 |
| 2-FNA | 0.30 | 0.10 | 0.08 | 0.12 | 0.08 | 0.04 | 0.08 |
| 2,6-Methyl-NA[d] | 0.01 | 0.06 | 0.07 | 0.07 | 0.06 | 0.07 | 0.08 |
| 2-NA | 0.00 | 0.00 | 0.06 | 0.06 | 0.00 | 0.10 | 0.10 |
| Dicarboxytetralin | 0.00 | 0.02 | 0.05 | 0.14 | 0.05 | 0.16 | 0.36 |
| Others | 0.39 | 0.42 | 0.25 | 0.31 | 0.35 | 0.17 | 0.21 |
| Total | 93.55 | 94.32 | 90.23 | 91.52 | 94.68 | 91.43 | 92.05 |
| Normalized % 2,6-NDA | 96.3 | 97.5 | 97.5 | 97.5 | 97.8 | 97.6 | 97.2 |
| Weight % Conversion | | | | | | | |
| TMLA | | 72.5 | 67.9 | 62.4 | 93.0 | 84.9 | 72.5 |
| Br-2,6-NDA | | 100.0 | 100.0 | 100.0 | 100.0 | 100.0 | 100.0 |
| 2-FNA | | 67.5 | 71.5 | 61.0 | 71.9 | 86.5 | 72.4 |

[a] Contained (Wt. %): Cobalt (0.125), manganese (0.75), bromine (0.373). Particle size of 20.9 (mean) and 24% less than 11 microns.
[b] 0.5 Weight percent palladium on carbon support
[c] Weight of total reactor effluent
[d] 2-Methyl-6-naphthoic acid

TABLE IV

| Run # | | | |
|---|---|---|---|
| Reactor Charge | | | |
| 2,6-NDA[a] (g) | | | 200 |
| Solvent Used (wt. %. Acetic acid/wt. %. water) | | | (90/10) |
| Solvent Wt. (g) | | | 1005 |
| Catalyst Used | | | 0.5% Pd/Carbon |
| Catalyst Wt. (g) | | | 4.5 |
| Catalyst Prior Uses | | | 0 |
| Conditions | | | |
| Temperature (°F.) | | | 595 |
| Pressure (psig) | | | 970 |
| Residence Time (min) | | | 120 |
| Hydrogen Pressure at Room Temp. (psig) | | | 50 |

| | Cake | Filtrate | Combined Products |
|---|---|---|---|
| Wt. % of Total | 88.8 | 11.20 | |
| Product Analysis (Wt. %) | | | |
| 2,6-NDA | 94.54 | 22.49 | 86.47 |
| 2,7-NDA | 0.00 | 0.16 | 0.02 |
| TMLA | 0.00 | 0.27 | 0.03 |
| Br-2,6-NDA | 0.03 | 0.03 | 0.03 |
| 2-FNA | 0.01 | 0.19 | 0.03 |
| 2-NA | 0.00 | 1.74 | 0.20 |
| Others | 0.37 | 25.75 | 3.21 |
| Total | 94.95 | 50.63 | 89.98 |
| Normalized %, 2,6-NDA | 99.57 | 44.42 | 96.10 |
| Metal Analysis (Wt. %) | | | |
| Cobalt | 0.01 | 0.80 | 0.10 |
| Manganese | 0.08 | 5.50 | 0.69 |
| Bromine | 0.03 | 2.82 | 0.34 |
| Wt. % Conversions | | | |
| TMLA | | | 98.6 |
| Br-2,6-NDA | | | 95.2 |
| 2-FNA | | | 88.5 |
| % Loss of Bromine | | | 8.1 |
| Particle Size | | | |
| Mean (microns) | 179 | | |
| % <11 microns | 0.3 | | |

[a] Same 2,6-NDA as reported in Table III. Mean particle size of 20.9 microns and 24 wt. percent of particles less than 11 microns.

TABLE V

| | 2,6-NDA Feed[a] | Example |
|---|---|---|
| Reactor Charge | | |
| 2,6-NDA[a] (g) | | 5.0 |
| Solvent Used (wt. % Acetic Acid/wt. % Water | | 0/100 |
| Solvent Weight (g) | | 25.0 |
| Catalyst Used | | |
| Catalyst Weight (g) | | 0.49 |
| Catalyst Previous Uses | | 6 |
| Conditions | | |
| Temperature (°F.) | | 600 |
| Pressure (psig) | | 1600 |
| Residence Time (min.) | | 10 |
| Hydrogen Pressure at Room Temperature (psig) | | 50 |
| Dry Product Analysis (wt %) | | |
| 2,6-NDA | 89.83 | 91.93 |
| 2,7-NDA | 0.00 | 0.00 |
| TMLA | 0.00 | 0.00 |
| Br-2,6-NDA | 4.30 | 0.02 |
| 2-FNA | 0.00 | 0.00 |
| 2-NA | 0.00 | 0.13 |
| Others[b] | 1.95 | 1.49 |
| Total | 93.08 | 93.57 |
| Normalized %, 2,6-NDA | 93.49 | 98.25 |
| Metals Analysis (wt %) | | |
| Cobalt | 0 | |
| Manganese | 0 | |
| Wt. Conversion | | |
| Br-2,6-NDA | | 99.5 |

[a] Used pure 2,6-NDA obtained by hydrolyzing highly pure dimethyl-2,6-naphthalenedicarboxylate.
[b] Impurities are monomethyl- and dimethyl-2,6-naphthalenedicarboxylate.

TABLE VI

| | 2,6-NDA Feed[a] | Run # 1 | 2 |
|---|---|---|---|
| Reactor Charge | | | |
| 2,6-NDA (g) | | 31.1 | 32.1 |
| Solvent Used (wt. % Acetic Acid/wt. % Water) | | 85/15 | 85/15 |
| Solvent Wt. (g) | | 88.8 | 91.6 |

TABLE VI-continued

| | 2,6-NDA Feed[a] | Run # 1 | Run # 2 |
|---|---|---|---|
| Catalyst Used | | 0.5% Pd/C | 0.5%/Pd/C |
| Catalyst Weight (g) | | 1.96 | 1.60 |
| Catalyst Previous Uses | | 0 | 4 |
| Conditions | | | |
| Temperature (°F.) | | 600 | 570 |
| Pressure (psig) | | 1070 | 840 |
| Residence Time (min.) | | 10 | 30 |
| Hydrogen Pressure at Room Temperature (psig) | | 300 | 300 |
| Dry Product Analysis (wt %) | | | |
| 2,6-NDA | 83.76 | 79.35 | 79.01 |
| 2,7-NDA | 0.00 | 0.01 | 0.01 |
| TMLA | 2.26 | 0.12 | 0.61 |
| Br-2,6-NDA | 1.84 | 0.19 | 0.24 |
| 2-FNA | 0.42 | 0.09 | 0.15 |
| 2-NA | 0.25 | 0.06 | 0.35 |
| Others | 2.39 | 2.93 | 3.14 |
| Total | 90.92 | 82.75 | 83.51 |
| Normalized %, 2,6-NDA | 92.12 | 95.90 | 94.62 |
| Metals Analysis (wt %) | | | |
| Cobalt | 0.68 | 0.57 | 0.67 |
| Manganese | 1.86 | 1.62 | 1.88 |
| Bromine | 1.84 | 1.51 | 1.76 |
| Wt. % Conversions | | | |
| TMLA | | 94.6 | 73.1 |
| Br-2,6-NDA | | 90.0 | 86.9 |
| 2-FNA | | 78.4 | 63.8 |
| % Loss of Bromine | | 17.9 | 4.3 |
| Particle Size | | | |
| Mean (microns) | | 263 | — |
| % <11 (microns) | | 0.4 | — |

TABLE VII

| | Starting Oxidation Reaction Mixture[a] | Run # 1 | 2 | 3 | 4 | 5 | 6 |
|---|---|---|---|---|---|---|---|
| Conditions | | | | | | | |
| Temperature (°F.) | | 575 | 600 | 650 | 575 | 600 | 650 |
| Residence Time (minutes) | | 10 | 10 | 10 | 30 | 30 | 30 |
| Shaking Speed (rpm) | | 360 | 360 | 360 | 360 | 360 | 360 |
| Analysis of Product | | | | | | | |
| Weight of Product (g) | | 20.14 | 20.13 | 20.09 | 20.04 | 20.23 | 20.06 |
| Weight Loss (gain) % | | (0.70) | (0.65) | (0.45) | (0.20) | (1.15) | (0.30) |
| Dry Down Weight (g) | | 5.16 | 5.13 | 5.15 | 5.19 | 5.19 | 5.19 |
| Mass Recovery (%) | | 99.7 | 99.1 | 99.5 | 100.3 | 100.2 | 100.3 |
| Analysis of Dry Product (wt %) | | | | | | | |
| TMLA[b] | 2.45 | 1.27 | 0.21 | 0.00 | 0.37 | 0.00 | 0.00 |
| TA[c] | 0.13 | 0.49 | 0.71 | 0.84 | 0.71 | 0.78 | 0.83 |
| IA[d] | 0.00 | 0.39 | 0.67 | 0.94 | 0.72 | 0.82 | 0.83 |
| 2,6-NDA | 87.40 | 86.99 | 88.51 | 87.12 | 84.63 | 87.19 | 86.90 |
| 2,7-NDA | 0.00 | 0.00 | 0.01 | 0.01 | 0.01 | 0.01 | 0.01 |
| Br-2,6-NDA | 1.74 | 0.50 | 0.20 | 0.09 | 0.15 | 0.13 | 0.06 |
| 2-FNA | 0.38 | 0.29 | 0.19 | 0.09 | 0.24 | 0.09 | 0.17 |
| 2-NA | 0.12 | 0.22 | 0.26 | 0.57 | 0.22 | 0.50 | 0.63 |
| Others | 2.51 | 1.74 | 1.99 | 3.65 | 1.65 | 2.67 | 3.48 |
| Total | 94.74 | 91.88 | 92.75 | 93.30 | 88.70 | 92.17 | 92.91 |
| Metals & Bromine Analysis (wt %) | | | | | | | |
| Bromine | 1.75 | 1.59 | 1.46 | 1.55 | 1.47 | 1.51 | 1.55 |
| Cobalt | 0.66 | 0.62 | 0.57 | 0.62 | 0.57 | 0.61 | 0.61 |
| Manganese | 1.81 | 1.70 | 1.57 | 1.73 | 1.62 | 1.70 | 1.70 |
| % Conversion (wt) | | | | | | | |
| TMLA | | 48.3 | 91.3 | 100.0 | 84.9 | 100.0 | 100.0 |
| Br-2,6-NDA | | 71.4 | 88.7 | 94.6 | 91.7 | 92.8 | 96.4 |
| 2-FNA | | 24.0 | 51.6 | 77.6 | 36.7 | 77.1 | 56.8 |

[a]The oxidation reaction mixture used for these runs was obtained from the continuous-mode, liquid phase oxidation of 2,6-dimethylnaphthalene. The charge of oxidation reaction mixture for each run weighed 20 grams and had the following analyses: 5.17 g of crude 2,6-NDA, 25.9 wt % solids 14.83 of liquid components and the liquid phase was 85 wt. % acetic acid and 15 wt. % water.
[b]Values are +/− 0.40.
[c]Terephthalic Acid
[d]Isophthalic Acid

TABLE VIII

| | Starting Oxid. Mixture[a] | Run # 1 | 2 | 3 | 4 | 5 | 6 | 7 | 8 | 9 | 10 |
|---|---|---|---|---|---|---|---|---|---|---|---|
| Reaction Conditions | | | | | | | | | | | |
| Diluent[b] | | none | none | none | none | none | none | A | A | A | W | A |
| Wt % Solids Present | | | 26 | 26 | 26 | 26 | 26 | 17 | 17 | 17 | 17 | 10 |
| Temperature (°F.) | | | 570 | 570 | 600 | 600 | 600 | 600 | 625 | 600 | 600 |
| Pressure (psig) | | | 800 | 800 | 1000 | 1000 | 1000 | 1000 | 1000 | 1300 | 1000 |
| Time (minutes) | | | 15 | 60 | 15 | 60 | 15 | 60 | 15 | 15 | 15 |
| After Hot Filtration at 200° F. | none | | | | | | | | | | |
| Wt % Solids Lost to Filtrate | | 8.3 | 10.7 | 10.4 | 12.3 | 11.7 | 11.5 | 14.3 | 12.9 | 13.1 | 14.1 |
| Wt % Liquid on Filter Cake | | 40 | 23 | 23 | 27 | 25 | 10 | 28 | 13 | 25 | 35 |
| Analysis of Dry Product[c] (wt %) | | | | | | | | | | | |
| TMLA[d] | 2.43 | 0.60 | 0.00 | 0.00 | 0.00 | 0.00 | 0.00 | 0.00 | 0.00 | 0.00 | 0.00 |
| TA | 0.13 | 0.01 | 0.19 | 0.21 | 0.18 | 0.18 | 0.07 | 0.09 | 0.09 | 0.03 | 0.04 |
| IA | 0.00 | 0.00 | 0.00 | 0.00 | 0.00 | 0.00 | 0.00 | 0.00 | 0.00 | 0.00 | 0.00 |
| 2,6-NDA | 87.27 | 94.91 | 97.62 | 97.40 | 96.31 | 94.21 | 97.10 | 96.12 | 95.07 | 98.08 | 96.96 |
| 2,7-NDA | 0.00 | 0.00 | 0.00 | 0.00 | 0.00 | 0.00 | 0.00 | 0.00 | 0.00 | 0.00 | 0.00 |

TABLE VIII-continued

| | Starting Oxid. Mixture[a] | Run # | | | | | | | | | |
|---|---|---|---|---|---|---|---|---|---|---|---|
| | | 1 | 2 | 3 | 4 | 5 | 6 | 7 | 8 | 9 | 10 |
| Br-2,6-NDA | 1.75 | 1.20 | 0.31 | 0.27 | 0.30 | 0.21 | 0.34 | 0.19 | 0.19 | 0.00 | 0.10 |
| 2-FNA | 0.39 | 0.25 | 0.10 | 0.07 | 0.09 | 0.05 | 0.14 | 0.06 | 0.08 | 0.13 | 0.08 |
| 2NA | 0.13 | 0.00 | 0.03 | 0.04 | 0.04 | 0.10 | 0.00 | 0.00 | 0.02 | 0.00 | 0.00 |
| Other Impurities | 2.38 | 0.60 | 0.71 | 0.56 | 0.50 | 0.54 | 0.77 | 0.65 | 0.61 | 0.70 | 0.58 |
| Total | 94.98 | 97.56 | 98.95 | 98.56 | 97.42 | 95.28 | 98.42 | 97.10 | 96.06 | 98.93 | 97.76 |
| Normalized 2,6-NDA (wt. %) | 92.37 | 97.28 | 98.66 | 98.83 | 98.86 | 98.88 | 98.66 | 98.99 | 98.97 | 99.14 | 99.18 |
| Metals & Bromine Analysis (wt %) | | | | | | | | | | | |
| Cobalt | 0.68 | 0.02 | 0.00 | 0.00 | 0.00 | 0.02 | 0.01 | 0.01 | 0.01 | 0.01 | 0.01 |
| Manganese | 1.83 | 0.26 | 0.02 | 0.02 | 0.01 | 0.05 | 0.02 | 0.03 | 0.04 | 0.02 | 0.02 |
| Bromine | 1.69 | 0.49 | 0.14 | 0.17 | 0.16 | 0.15 | 0.20 | 0.13 | 0.17 | 0.07 | 0.11 |
| TMLA | | 75 | 100 | 100 | 100 | 100 | 100 | 100 | 100 | 100 | 100 |
| Br-2,6-NDA | | 32 | 83 | 84 | 83 | 88 | 81 | 89 | 89 | 100 | 94 |
| 2-FNA | | 36 | 76 | 81 | 76 | 87 | 65 | 85 | 79 | 68 | 79 |
| Other Impurities | | 75 | 70 | 76 | 79 | 77 | 68 | 73 | 74 | 71 | 76 |
| Cobalt | | 97 | >99 | >99 | >99 | 98 | 99 | 99 | 98 | 99 | 99 |
| Manganese | | 86 | 99 | 99 | 99 | 97 | 99 | 98 | 98 | 99 | 99 |
| Bromine | | 71 | 91 | 90 | 91 | 91 | 88 | 92 | 90 | 96 | 94 |
| Particle Size After Hot Filtration | | | | | | | | | | | |
| Mean (microns) | 61 | 22 | 212 | 140 | 179 | 159 | 200 | 262 | 142 | 217 | 143 |
| % Fine <11 microns | 18 | 20 | 10 | 12 | 12 | 9 | 6 | 8 | 11 | 0 | 4 |

[a] Oxidation reaction mixture used for these runs was obtained from a continuous oxidation of 2,6-dimethylnaphthalene. The mixture contained 26 wt. % solids in an 85 wt. % acetic acid/15 wt. % water mixture.
[b] W = Water, A = 85 wt. % acetic acid/15 wt. % water.
[c] After hot filtration, solid filter cake was washed with an 85 wt. % acetic acid/15% wt. water mixture at 200° F. The amount of wash solvent was twice the weight of the filter cake.
[d] Values are +/−0.10.

TABLE IX

| | Starting Mixture[a] (Feedstock) | Run # | | | | | | | |
|---|---|---|---|---|---|---|---|---|---|
| | | 1[b] | | 2[b] | | 3[b] | | 4[b] | |
| Reaction Conditions[a] | none[d] | | | | | | | | |
| Temperature (°F.) | | 600 | | 600 | | 625 | | | |
| Residence Time (minutes) | | 15 | | 15 | | 15 | | | |
| Cooling Rate (°F./minute to 550° F.) | | 6.3 | | 2.5 | | 7.9 | | | |
| Weight Percent | | | | | | | | | |
| Solvent in Wet Cake | 34.3 | 10 | | 16 | | 13 | | | |
| Product in Filtrate | 8.2 | 11.5 | | 12.0 | | 12.9 | | | |
| Mass Balance | 99.4 | 99.0 | | 97.4 | | 100.3 | | | |
| Total Solvent on Cake | 10.2 | 2.5 | | 4 | | 3.3 | | | |
| Solids in Feed to Filter | 17.6 | 20.2 | | 19.3 | | 19.5 | | | |

| Analysis of Dry Feedstock Solids, Filter Cake, and Filtrate | Starting Mixture[a] (Feedstock) | 1 | | 2 | | 3 | | 4 | |
|---|---|---|---|---|---|---|---|---|---|
| | | Cake | Filtrate | Cake | Filtrate | Cake | Filtrate | Cake | Filtrate |
| Metals and Bromine (wt %) | | | | | | | | | |
| Br | 1.84 | 0.64 | 12.10 | 0.34 | 9.20 | 0.32 | 9.90 | 0.22 | 9.3 |
| Co | 0.68 | 0.10 | 6.00 | 0.08 | 3.75 | 0.06 | 4.10 | 0.05 | 3.88 |
| Mn | 1.86 | 0.60 | 14.00 | 0.21 | 11.30 | 0.17 | 12.10 | 0.12 | 11.4 |
| Organic Compounds (wt %) | | | | | | | | | |
| TMLA[e] | 2.26 | 1.24 | 9.65 | 0.00 | 0.68 | 0.00 | 0.36 | 0.00 | 0.03 |
| TA | 0.00 | 0.03 | 1.58 | 0.18 | 6.75 | 0.15 | 7.18 | 0.16 | 6.08 |
| IA | 0.00 | 0.00 | 0.00 | 0.00 | 7.24 | 0.00 | 7.29 | 0.00 | 6.97 |
| 2,6-NDA | 83.76 | 87.34 | 2.06 | 94.89 | 4.80 | 98.23 | 4.02 | 86.75 | 3.64 |
| Br-2,6-NDA | 1.84 | 1.17 | 4.79 | 0.35 | 0.01 | 0.27 | 0.00 | 0.16 | 0.03 |
| 2-FNA | 0.42 | 0.20 | 1.05 | 0.15 | 0.78 | 0.15 | 0.31 | 0.11 | 0.49 |
| 2-NA | 0.25 | 0.00 | 1.72 | 0.00 | 2.64 | 0.00 | 2.69 | 0.00 | 3.20 |
| Others | 2.39 | 0.80 | 22.71 | 0.91 | 14.61 | 0.96 | 16.81 | 1.05 | 15.78 |
| Total | 90.92 | 90.78 | 43.56 | 96.48 | 37.50 | 99.77 | 38.66 | 88.23 | 36.19 |
| Normalized 2,6-NDA (wt %) | 92.12 | 96.21 | 4.73 | 98.35 | 12.81 | 98.46 | 10.38 | 98.32 | 10.05 |

| | Starting Mixture | Run # | | | |
|---|---|---|---|---|---|
| | | 1 | 2 | 3 | 4 |
| Particle Size of Cake Sample | | | | | |
| Mean (microns) | 24[f] | | 200[g] | 166[g] | 142[g] |
| (% <11 microns) | 20[f] | | 6.2[g] | 13.7[g] | 11.3[g] |
| Filter Cake Analysis (wt % Removal of Impurities Relative to Feedstock) | | | | | |
| Br | | 65.2 | 81.5 | 82.8 | 87.9 |
| Co | | 85.3 | 88.8 | 90.7 | 93.4 |
| Mn | | 67.7 | 88.8 | 90.7 | 93.4 |
| TMLA | | 45.2 | 100.0 | 100.0 | 100.0 |
| 2,6-NDA | | 0.2 | 0.6 | 0.5 | 0.5 |
| Br-2,6-NDA | | 36.4 | 81.2 | 85.3 | 91.3 |
| FNA | | 52.5 | 63.8 | 63.8 | 73.9 |
| 2-NA | | 100.0 | 100.0 | 100.0 | 100.0 |

TABLE IX-continued

| | | | | |
|---|---|---|---|---|
| Others | 66.4 | 61.8 | 59.7 | 56.0 |
| Total Product Accountability (Cake and Filtrate) % Converted (or Lost) From Feedstock | | | | |
| TMLA | 14.8 | 96.5 | 98.1 | 99.8 |
| Br-2,6-NDA | 20.3 | 83.3 | 87.1 | 92.2 |
| 2-FNA | 35.8 | 46.5 | 59.1 | 62.1 |
| Br | 14.1 | 26.1 | 20.3 | 24.2 |
| Mn | 8.7 | 20.2 | 13.8 | 15.2 |
| Co | 14.1 | 26.7 | 19.5 | 20.6 |

*See footnote a) Table VIII
*Sample Filtered hot at 200° F. Filter cake was not washed to simulate operating with a "solid bowl" centrifuge.
*Starting mixture for Runs 1-4 was diluted to a 5:1 weight ratio of liquid to solids. A mixture of 85% acetic acid and 15% water (wt) was used for the dilution.
*No heating at elevated temperature - only hot filtration of diluted oxidation reaction mixture.
*Values are +/−0.10.
*Centrifuged solids from untreated starting mixture.
*Cake sample.

Only certain embodiments of the invention have been set forth and alternative embodiments and various modifications will be apparent from the above description to those skilled in the art. These and other alternatives are considered equivalents and within the spirit and scope of the present invention.

Having described the invention, that which is claimed is:

1. A method for preparing an aromatic carboxylic acid comprising a) oxidizing in the liquid phase an aromatic compound having at least one oxidizable alkyl or acyl group with an oxygen-containing gas, in a solvent comprising a low molecular weight carboxylic acid, in the presence of a oxidation catalyst comprising heavy metal components, and at a reaction temperature of about 250° F. to about 450° F., thereby forming an oxidation reaction product mixture comprising an aromatic carboxylic acid; subsequently b) heating the oxidation reaction product mixture at a temperature of at least about 550° F. thereby forming a second product mixture; and c) recovering from the second product mixture the aromatic carboxylic acid.

2. The method of claim 1 wherein in step b) the temperature is at least about 600° F.

3. The method of claim 1 wherein the aromatic compound is 2,6-dimethylnaphthalene and the aromatic carboxylic acid is 2,6-naphthalenedicarboxylic acid.

4. The method of claim 1 wherein the oxidation catalyst comprises cobalt, manganese and bromine components.

5. The method of claim 3 wherein the reaction temperature in step a) is about 350° F. to about 420° F.

6. The method of claim 1 wherein the solvent in step a) comprises acetic acid.

7. The method of claim 1 wherein in step b) at least about 10 weight percent of the aromatic carboxylic acid present is in solution.

8. The method of claim 1 wherein the oxidation product mixture comprises 2,6-naphthalenedicarboxylic acid and trimellitic acid, and wherein in step b) the amount of the trimellitic acid in the oxidation reaction mixture is decreased by at least about 20 percent.

9. The method of claim 1 wherein step a) and step b) are conducted in separate reaction zones.

10. The method of claim 1 wherein recovering in step c) comprises partitioning solid aromatic carboxylic acid from the second product mixture forming partitioned aromatic carboxylic acid and mother liquor.

11. The method of claim 10 wherein at least part of the mother liquor is recycled to step a).

12. The method of claim 1 wherein the recovery in step c) comprises cooling the second product mixture to a temperature of no more than about 450° F. at a cooling rate of no more than about 80° F. per minute and subsequently partitioning solid aromatic carboxylic acid from the cooled second product mixture.

13. The method of claim 1 further comprising, d) esterifying the aromatic carboxylic acid recovered in step c) with a low molecular weight alcohol to form the corresponding aromatic carboxylic acid ester.

14. The method of claim 13 further comprising, e) purifying the aromatic carboxylic acid ester and recycling to step b) impurities isolated during the purifying.

15. The method of claim 9 wherein vaporized solvent formed during the oxidation reaction in step a) is at least in part added to the reaction zone used for step b).

16. The method of claim 1 wherein the aromatic compound is p-xylene and the aromatic carboxylic acid is terephthalic acid.

17. The method of claim 1 wherein the aromatic compound is m-xylene and the aromatic carboxylic acid is isophthalic acid.

18. A method for preparing an aromatic carboxylic acid comprising a) oxidizing in the liquid phase an aromatic compound having at least one oxidizable alkyl or acyl group with an oxygen-containing gas, in a solvent comprising a low molecular weight carboxylic acid, in the presence of an oxidation catalyst comprising heavy metal components, and at a reaction temperature of about 250° F. to about 450° F., thereby forming an oxidation reaction product mixture comprising an aromatic carboxylic acid; subsequently b) heating the oxidation reaction product mixture in the presence of an added solvent comprising water or a lower molecular weight carboxylic acid at a temperature of at least about 500° F., thereby forming a second product mixture; and c) recovering from the second product mixture the aromatic carboxylic acid.

19. The method of claim 18 wherein the added solvent in step b) comprises water.

20. The method of claim 18 wherein the aromatic carboxylic acid is 2,6-naphthalenedicarboxylic acid.

21. A method for preparing an aromatic carboxylic acid comprising a) oxidizing in the liquid phase an aromatic compound having at least one oxidizable alkyl or acyl group with an oxygen-containing gas, in a solvent comprising a low molecular weight carboxylic acid, in the presence of an oxidation catalyst comprising heavy metal components, and at a reaction temperature of about 250° F. to about 450° F., thereby forming an oxidation reaction product mixture comprising an aromatic carboxylic acid; subsequently b) heating the oxidation reaction product mixture at a temperature of at least 500° F. in the presence of hydrogen gas and a hydrogenation catalyst.

22. The method of claim 21 wherein the hydrogenation catalyst comprises at least one supported Group VIII noble metal.

23. The method of claim 21 wherein the aromatic carboxylic acid is 2,6-naphthalenedicarboxylic acid.

* * * * *

UNITED STATES PATENT AND TRADEMARK OFFICE
CERTIFICATE OF CORRECTION

PATENT NO. : 5,292,934
DATED : March 8, 1994
INVENTOR(S) : David L. Sikkenga, et al It is certified that error appears in the above-indentified patent and that said Letters Patent is hereby corrected as shown below:

| Col. | Line | |
|---|---|---|
| 5 | 35 | "cobalt an manganese" should read --cobalt and manganese-- |
| 5 | 36 | "The bromine is released" should read --The bromine ion released-- |
| 5 | 38 | "conditions of be readily determined" should read --conditions can be readily determined-- |

Signed and Sealed this

Twenty-sixth Day of July, 1994

Attest:

BRUCE LEHMAN

Attesting Officer    Commissioner of Patents and Trademarks